US009598799B2

(12) United States Patent
Shoshani et al.

(10) Patent No.: US 9,598,799 B2
(45) Date of Patent: *Mar. 21, 2017

(54) METHODS FOR STABILIZING PHYSICAL DIMENSIONS AND POSITIONING OF KNITTED ELECTRODES OF A KNITTED GARMENT

(71) Applicant: HEALTHWATCH LTD., Herzliya (IL)

(72) Inventors: Boaz Shoshani, Raanana (IL); Uri Amir, Or Yehuda (IL)

(73) Assignee: HEALTHWATCH LTD., Herzeliya (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/203,690

(22) Filed: Jul. 6, 2016

(65) Prior Publication Data
US 2016/0310076 A1    Oct. 27, 2016

Related U.S. Application Data

(63) Continuation-in-part of application No. 14/767,563, filed as application No. PCT/IL2014/050134 on Feb. 7, 2014, now Pat. No. 9,416,470.
(Continued)

(51) Int. Cl.
*D04B 1/24* (2006.01)
*A61B 5/00* (2006.01)
(Continued)

(52) U.S. Cl.
CPC ............ *D04B 1/246* (2013.01); *A61B 5/0006* (2013.01); *A61B 5/0402* (2013.01);
(Continued)

(58) Field of Classification Search
CPC . D04B 1/246; D04B 1/18; D04B 1/24; D04B 1/16; D04B 1/22; D04B 7/16;
(Continued)

(56) References Cited

U.S. PATENT DOCUMENTS

| | | | |
|---|---|---|---|
| 5,282,846 | A | 2/1994 | Schmitt |
| 5,412,957 | A | 5/1995 | Bradberry et al. |

(Continued)

FOREIGN PATENT DOCUMENTS

| | | |
|---|---|---|
| CA | 2050030 A1 | 3/1992 |
| EP | 1449946 A1 | 8/2004 |

(Continued)

OTHER PUBLICATIONS

David J. Spencer, "Knitting Technology: A Comprehensive Handbook and Practical Guide," vol. 16 of Woodhead Publishing Series in Textiles, CRC Press. 2001, 9.4 The float stitch (p. 92).

(Continued)

*Primary Examiner* — Danny Worrell
(74) *Attorney, Agent, or Firm* — Troutman Sanders LLP

(57) ABSTRACT

A method for stabilizing the physical dimensions and positioning of at least one selected textile region of a knitted garment. The method includes producing the garment including a conductive textile electrode, rigidifying the at least one selected textile region and knitting a preconfigured region proximal to the at least one selected textile region with a lower knitting density than the preconfigured density of the tubular form. The invention further provides a garment having a tubular form, knitted by a seamless knitting machine with base-yarns. The garment includes at least one conductive textile electrode. The garment further includes at least one preconfigured region in proximity to the at least one selected textile region, having a lower knitting density than the preconfigured density of the tubular form and the at least one selected textile region.

20 Claims, 3 Drawing Sheets

Related U.S. Application Data

(60) Provisional application No. 61/771,874, filed on Mar. 3, 2013, provisional application No. 61/763,963, filed on Feb. 13, 2013.

(51) Int. Cl.
*A61B 5/0402* (2006.01)
*A61B 5/0408* (2006.01)
*D04B 1/18* (2006.01)
*B32B 27/12* (2006.01)

(52) U.S. Cl.
CPC ........ *A61B 5/04085* (2013.01); *A61B 5/6804* (2013.01); *B32B 27/12* (2013.01); *D04B 1/18* (2013.01); *D04B 1/24* (2013.01); *A61B 2562/125* (2013.01); *B32B 2535/00* (2013.01)

(58) Field of Classification Search
CPC .. D04B 7/30; D04B 9/42; B32B 27/12; B32B 5/026; A61B 5/04085
See application file for complete search history.

(56) References Cited

U.S. PATENT DOCUMENTS

| | | |
|---|---|---|
| 5,509,931 A | 4/1996 | Schmitt |
| 7,135,227 B2 | 11/2006 | Karayianni et al. |
| 7,348,285 B2 | 3/2008 | Dhawan et al. |
| 7,559,902 B2 | 7/2009 | Ting et al. |
| 7,849,888 B2 | 12/2010 | Karayianni et al. |
| 7,926,254 B2 | 4/2011 | Karayianni et al. |
| 8,032,199 B2 | 10/2011 | Linti et al. |
| 8,171,755 B2 | 5/2012 | Jahn et al. |
| 8,443,634 B2 | 5/2013 | Scheffler et al. |
| 2004/0057176 A1 | 3/2004 | Dhawan et al. |
| 2006/0281282 A1 | 12/2006 | Chu et al. |
| 2008/0091097 A1 | 4/2008 | Linti et al. |
| 2008/0287022 A1 | 11/2008 | Dhawan et al. |
| 2009/0018428 A1 | 1/2009 | Dias et al. |
| 2009/0159149 A1 | 6/2009 | Karayianni et al. |
| 2010/0208445 A1 | 8/2010 | Asvadi et al. |
| 2011/0132040 A1 | 6/2011 | Jahn et al. |
| 2011/0259638 A1 | 10/2011 | Sherrill et al. |
| 2012/0117707 A1 | 5/2012 | Gay |
| 2014/0070957 A1 | 3/2014 | Longinotti-Buitoni et al. |
| 2014/0135608 A1 | 5/2014 | Gazzoni |

FOREIGN PATENT DOCUMENTS

| | | |
|---|---|---|
| WO | 2004097089 A1 | 11/2004 |
| WO | 2005032447 A3 | 4/2005 |
| WO | 2012104826 A1 | 8/2012 |
| WO | 2012140522 A3 | 10/2012 |

OTHER PUBLICATIONS

Niir Board. The Complete Technology Book on Textile Spinning, Weaving, Finishing and Printing; National Institute of Industrial Re, 2009, p. 251—float loop.
International Preliminary Report on Patentability for International Application No. PCT/IL2014/050134, dated Jan. 22, 2015.

Detailed A

US 9,598,799 B2

METHODS FOR STABILIZING PHYSICAL DIMENSIONS AND POSITIONING OF KNITTED ELECTRODES OF A KNITTED GARMENT

CROSS REFERENCE TO RELATED APPLICATIONS

This application is a Continuation-In-Part of U.S. patent application Ser. No. 14/767,563, filed Aug. 12, 2015, which is National Phase patent application of International Application No. PCT/IL2014/050134, filed Feb. 7, 2014, which claims the benefit under 35 U.S.C. §119(e) to U.S. Provisional Application No. 61/763,963, filed Feb. 13, 2013, and U.S. Provisional Application No. 61/771,874, filed Mar. 3, 2013, the disclosures of each of which are incorporated herein by reference in their entirety.

FIELD OF THE INVENTION

The present invention relates to knitted fabrics and more particularly, the present invention relates to wearable health monitoring systems, having knitted electrodes, wherein the knitted electrodes and the knitted fabric in the vicinity of the knitted electrodes are devised to maintain substantially steady dimensions, a substantially steady distance from each other, in particular between horizontally adjacent electrodes, and to maintain substantially steady bodily position with respect to the skin of the wearer.

BACKGROUND OF THE INVENTION AND PRIOR ART

Knitted electrodes in the garment are made of conductive yarn, which conductive yarn is knitted together with other basic yarns such as Nylon, bare spandex, covered spandex and/or other types of yarn.

The positioning of an electrode against a monitored living body is of critical importance for obtaining proper ECG signals, especially when the monitored living body is in motion. Moreover, the repeatability of the electrodes location on the body is of critical importance for comparing ECG signals in separate measurement sessions.

When designing a knitted ECG garment, there is a need to ensure that the electrodes are repeatably positioned at the same respective pre-configured positions with respect to the monitored living body, for a given garment size designated to be worn by a variety of people. Usually, people of the same size have different body structure, weight and height, which may affect the respective position of the electrodes on their body, though the garment is of the same size.

Being knitted in a fabric, the electrodes gain a natural stretch, which stretch may affect the quality by introducing artifacts and damage the repeatability of the recorded ECG signals. Furthermore, garment being knitted, and thereby stretchable, may cause the electrodes to move with respect to the adjacent skin of the wearer, which may further affect the quality by introducing artifacts and damage the repeatability of the recorded signals. These damaging artifacts may occur because of changes in the electrode electrical characteristics, and may cause unnecessary noises in the system during breathing and bodily motions, wherein the spatial positioning of an electrode, with respect to the monitored organ, may change.

There is a need to stabilize the bodily position of the sensing knitted electrodes with respect to the skin of the wearer, in order to obtain a stable signal through the skin, the skin having a high impedance. In order to achieve a stable biological signal (such as ECG) reading, one needs to establish a stable interface between the electrodes and the skin of the wearer. The biological signal source needs to face stable resistance values that have only small variations as a result of breathing or shifting in the electrode position relative to the biological signal source.

In electric terms, the voltage sensed by the electrode can be represented by: $E = I \times Z$. When the electrical impedance Z is substantially constant, as desired, the voltage E measured by the electrode depends only on changes of the current I and that is exactly what we want to measure. That is, the electrode size or re-positioning should not affect the measurement of voltage E. we want to sense only the signal changes that result from the biological changes such as the heart activity, when measuring ECG.

By the retention of physical dimensions, that is area size and impedance, of the knitted electrode, one can obtain a signal that is not affected by changes damaging artifact but a signal representing only the physiological changes of the body.

There is therefore a need and it would be advantageous to have methods for knitting a garment such that the elasticity of one or more selected regions is stabilized, for example by rigidifying the selected regions and thereby maintain the original dimensions of these regions. Furthermore, there is a need for a stable and repeatable positioning of electrodes at respective pre-configured bodily location, which positioning is of extreme importance to obtain good ECG signals, facilitating clinical level ECG, while the monitored person is either in rest or is moving, jumping or walking.

It should be noted that the term "ECG signals", as used herein, refers to any physiological signal of the monitored living being that can be sensed directly or indirectly by an electrode, including signals for ECG analysis.

The terms "underwear" or "garment", as used herein with conjunction with wearable clothing items, refers to seamless wearable clothing items that preferably, can be tightly worn adjacently to the body of a monitored living being, typically adjacently to the skin, including undershirts, sport shirts, brassiere, underpants, special hospital shirts, socks and the like. Typically, the terms "underwear" or "garment" refer to a clothing item that is worn adjacently to the external surface of the user's body, under external clothing or as the only clothing, in such a way that the fact that there are sensors embedded therein, is not seen by any other person in regular daily behavior. An underwear item may also include a clothing item that is not underwear per se, but still is in direct and preferably tight contact with the skin, such as a T-shirt, sleeveless or sleeved shirts, sport-bra, tights, dancing-wear, and pants. The sensors, in such a case, can be embedded in such a way that they remain unseen by external people to comply with the "seamless" requirement.

The phrase "clinical level ECG", as used herein with conjunction with ECG measurements, refers to the professionally acceptable number of leads, sensitivity and specificity needed for a definite conclusion by most cardiology physicians to suspect a risky cardiac problem (for example, arrhythmia, myocardial ischemia, heart failure) that require immediate further investigation or intervention. Currently, it is at least a 12-leads ECG and preferably 15-lead ECG, coupled with a motion/posture compensation element, and a real-time processor with adequate algorithms.

The phrase "base-yarn", as used herein, refers to the yarn from which the fabric of the garment is knitted. The fabric is typically knitted with Nylon, bare Spandex and covered spandex. In another example embodiment, the fabric is typically knitted with a base-yarn such as Nylon and covered spandex. It should be noted that such a garment can be knitted with any type of base-yarn, including Nylon yarn textured or flat, selected types of Nylons, Polyester, Polypropylene, Acetate, manmade fibers, natural yarns like cotton, bamboo, wool, and blends of the mentioned raw materials. Selection of yarn is also based on fabric weight, body size for men and women, fabric weight and design requirements.

BRIEF SUMMARY OF THE INVENTION

It is an intention of the present invention to provide methods for knitting a garment such that the elasticity of one or more selected regions is prevented or at least limited and thereby substantially maintaining the original dimensions of these regions.

It should be noted that the present invention will be described in terms of the regions, in which regions' elasticity is substantially prevented or at least limited, being knitted electrodes, but these regions are not limited to being knitted electrodes, and may be any knitted region in a knitted fabric.

Knitted electrodes in a garment are made of conductive yarn, which conductive yarn is knitted together with other basic yarns such as Nylon, bare spandex, covered spandex and/or other types of synthetic, manmade, or natural yarn.

It is an intention of the present invention to provide methods for obtaining stable and repeatable positioning of electrodes at respective pre-configured bodily location, which positioning is of extreme importance to obtain good ECG signals, facilitating clinical level ECG, while the monitored person is either in rest or is moving, including running, jumping or walking. It is the intention of the present invention to ensure that the ECG signals are obtained from substantially the same location on the monitored body.

Once the exact locations of electrodes: RA, LA, V1, V2, V3, V4, V5, V6, RL and LL, and optionally, V7, V8 and V9, are selected for each garment size, the electrodes are knitted with their special knitting construction using a conductive yarn having a preconfigured distance from each other.

It is an intention of the present invention to provide methods for maintaining this substantially fixed distance between each of the electrodes, even when the garment is stretched during wearing or the wearer is in motion.

According to teachings of the present invention, there is provided a method for substantially reducing the elasticity of at least one selected textile region of a knitted garment, the method including the steps of knitting the garment in a tubular form with a preconfigured knitting density, wherein at least one conductive textile electrode is integrally knitted into the garment, while knitting the garment, and rigidifying the at least one selected textile region. The rigidifying process includes applying rigidifying matter onto and/or into the at least one selected textile region, thereby substantially reducing the elasticity of said at least one selected textile region.

Preferably, the textile electrode is knitted with higher knitting density than the preconfigured knitting density of the tubular form.

Typically, with no limitations, the at least one selected textile region is the at least one conductive textile electrode.

The at least one selected textile region is selected from the group consisting of a conductive textile electrode and a region of the garment situated between two adjacent textile electrodes.

Typically, with no limitation, the garment and the at least one conductive textile electrode are produced by a knitting machine such as a Santoni knitting machine or an equivalent machine.

Optionally, the rigidifying matter is thermoplastic polyurethane (TPU), wherein the TPU is laminated over the external surface of the at least one selected textile region.

Optionally, the rigidifying matter is fusible knitting yarn having a low melting point, wherein the fusible yarn is knitted over the external surface of the at least one selected textile region. When the fabric of the garment is dyed, the fusible yarn melts and thereby creates a stable and rigidified area.

Optionally, the rigidifying matter is a non-elastic knitting yarn having no or limited elasticity, wherein a frame, having a preconfigured width, is knitted around the at least one conductive textile electrode, using the non-elastic yarn.

Optionally, the rigidifying matter is a non-elastic yarn having no or limited elasticity, wherein the non-elastic yarn is sewn over the at least one selected textile region.

Optionally, the rigidifying matter is a non-elastic knitting yarn having no or limited elasticity, wherein the non-elastic yarn is knitted in a region of the garment between two adjacent textile electrodes.

Optionally, the rigidifying matter is a non-elastic yarn having no or limited elasticity, and wherein said non-elastic yarn is sewn over said at least one selected textile region.

Optionally, the rigidifying matter is a cross polymer lubricant, wherein the cross polymer lubricant is spayed over the at least one selected textile region.

According to further teachings of the present invention, there is provided a method for substantially reducing the elasticity of at least one selected textile region of a knitted garment. The method includes knitting the garment in a tubular form, wherein at least one conductive textile electrode is integrally knitted into the garment, while knitting the garment; rigidifying the at least one selected textile region, thereby substantially reducing the elasticity of said at least one selected textile region; and knitting a preconfigured region proximal to the at least one selected textile region with a lower knitting density than said preconfigured density of said tubular form, to thereby form a loosened region the preconfigured region that is in proximity to the at least one conductive textile electrode.

The rigidifying process may include applying rigidifying matter onto and/or into the at least one selected textile region, thereby substantially reducing the elasticity of the at least one selected textile region.

Optionally, the rigidifying matter is thermoplastic polyurethane (TPU), wherein the TPU is laminated over the external surface of the at least one selected textile region.

Optionally, the rigidifying matter is fusible knitting yarn having a low melting point, wherein the fusible yarn is knitted over the external surface of the at least one selected textile region. When the fabric of the garment is dyed, the fusible yarn melts and thereby creates a stable and rigidified area.

Optionally, the rigidifying matter is a non-elastic knitting yarn having no or limited elasticity, wherein a frame, having a preconfigured width, is knitted around the at least one conductive textile electrode, using the non-elastic yarn.

The at least one selected textile region is selected from the group consisting of a conductive textile electrode and a region of the garment situated between two adjacent textile electrodes.

Typically, with no limitation, the garment and the at least one conductive textile electrode are produced by a knitting machine such as a Santoni knitting machine or an equivalent machine.

Optionally, the rigidifying matter is a non-elastic yarn having no or limited elasticity, wherein the non-elastic yarn is sewn over the at least one selected textile region.

Optionally, the rigidifying matter is a non-elastic knitting yarn having no or limited elasticity, wherein the non-elastic yarn is knitted in a region of the garment between two adjacent textile electrodes.

Optionally, the rigidifying matter is a cross polymer lubricant, wherein the cross polymer lubricant is spayed over the at least one selected textile region.

Optionally, the method further comprising the step of modifying the elasticity of at least one other selected region of the garment.

Typically, with no limitations, the at least one selected textile region is the at least one conductive textile electrode.

Typically, with no limitations, the rigidifying process includes knitting the garment with a preconfigured knitting density, wherein the at least one textile electrode is knitted with higher knitting density than the preconfigured knitting density of the tubular form.

According to further teachings of the present invention, there is provided a method for knitting a garment having a tubular form being knitted with a base-yarn, including knitting at least one conductive textile electrode, using a knitting machine having N participating feeders and M needles. The method includes the steps of continuously knitting the tubular form with one or more flexible non-conductive base-yarns and with a preconfigured knitting density, and knitting the at least one textile electrode integrally within the tubular form, using a conductive yarn, in addition to the non-conductive yarns.

The conductive yarn is knitted in a float-loop form by knitting a stitch and skipping over y needles, as follows:
  a) continue knitting with at least one base-yarn, when start knitting a current line segment of a conductive textile electrode, preferably in a knit-and-miss knitting scheme.
  b) knitting a line segment $L_k$, using feeder $F_i$ and start stitching with needle $D_j$.
  c) knitting line the next segment $L_{k+1}$, using the next feeder $F_{i+1}$ and start stitching the first float-loop with needle $D_{j+s}$, where 0<s<y.
  d) repeat steps (i) and (ii) for N feeders and for a preconfigured number of line segments, wherein each line segment has a preconfigured length.
  e) resume knitting with the base-yarns, when completed knitting the current line segment.

The float-loops are knitted in a shifted needle knitting scheme, together with unique digital knitting density control, to thereby improve the pressure and the tightness of the at least one conductive textile electrode to the skin of the user.

A preconfigured region, proximal to the at least one conductive textile electrode, is knitted with a lower knitting density than the preconfigured density of the tubular form, to thereby form a loosened knitted fabric in that region being in proximity to the at least one conductive textile electrode.

The knit-and-miss scheme is selected from the group of knitting schemes including:
  a) knit-one-and-miss-one knitting pattern.
  b) knit-two-and-miss-one knitting pattern.
  c) knit-one-and-miss-two knitting pattern.

Optionally, a preconfigured region of the tubular form, disposed around and adjacently to the at least one textile electrode, is knitted with higher knitting density than the preconfigured knitting density of the tubular form.

According to further teachings of the present invention, there is provided a garment having a tubular form, being knitted by a seamless knitting machine with base-yarns, the garment including at least one conductive textile electrode, the at least one conductive textile electrode including a multiplicity of knitted line segments, each knitted with a conductive yarn and a spandex yarn, wherein the spandex yarn is knitted continuously.

The tubular form is knitted with a preconfigured knitting density. A preconfigured region, proximal to the at least one conductive textile electrode, is knitted with a lower knitting density than the preconfigured density of the tubular form, to thereby form a loosened knitted fabric in that region being in proximity to the at least one conductive textile electrode.

At least one of the base-yarns continues knitting when the knitting a current line segment of a conductive textile electrode begins, preferably in a knit-and-miss knitting scheme.

Preferably, the conductive yarn has a float-loop form, forming a multiplicity of the float-loops, wherein each of the float-loops is knitted by skipping over y needles between consecutive stitches. A given line segment starts stitching by needle $D_j$, and the next line segment starts stitching by needle $D_{j+s}$, where 0<s<y.

Preferably, the textile electrode is knitted with higher knitting density than the preconfigured knitting density of the tubular form.

Optionally, at least one selected textile region of the garment is rigidified by applying rigidifying matter onto or into the at least one selected textile region, wherein the at least one selected textile region is selected from the group consisting of a conductive textile electrode and a region of the garment situated between two adjacent textile electrodes.

Optionally, the at least one selected textile region is rigidified using TPU, and wherein the TPU is laminated over the external surface of the at least one selected textile region.

Optionally, the at least one selected textile region is rigidified using fusible yarn having a low melting point, wherein the a fusible yarn is knitted over the external surface of the at least one selected textile region, and when the garment is dyed, the fusible yarn melts and thereby creates a stable and rigidified area.

Optionally, the at least one selected textile region is rigidified using a non-elastic yarn having no or limited elasticity, wherein a frame, having a preconfigured width, is knitted around the at least one conductive textile electrode, using the non-elastic yarn.

Optionally, the at least one selected textile region is rigidified using a non-elastic yarn having no or limited elasticity, wherein the non-elastic yarn is knitted in the region of the garment between two adjacent textile electrodes.

Optionally, the rigidifying matter is a cross polymer lubricant, and wherein the cross polymer lubricant is sprayed over in the at least one selected textile region.

BRIEF DESCRIPTION OF THE DRAWINGS

The present invention will become fully understood from the detailed description given herein below and the accompanying drawings, which are given by way of illustration and example only and thus not limitative of the present invention, and wherein.

DETAILED DESCRIPTION OF THE INVENTION

Figure 1:
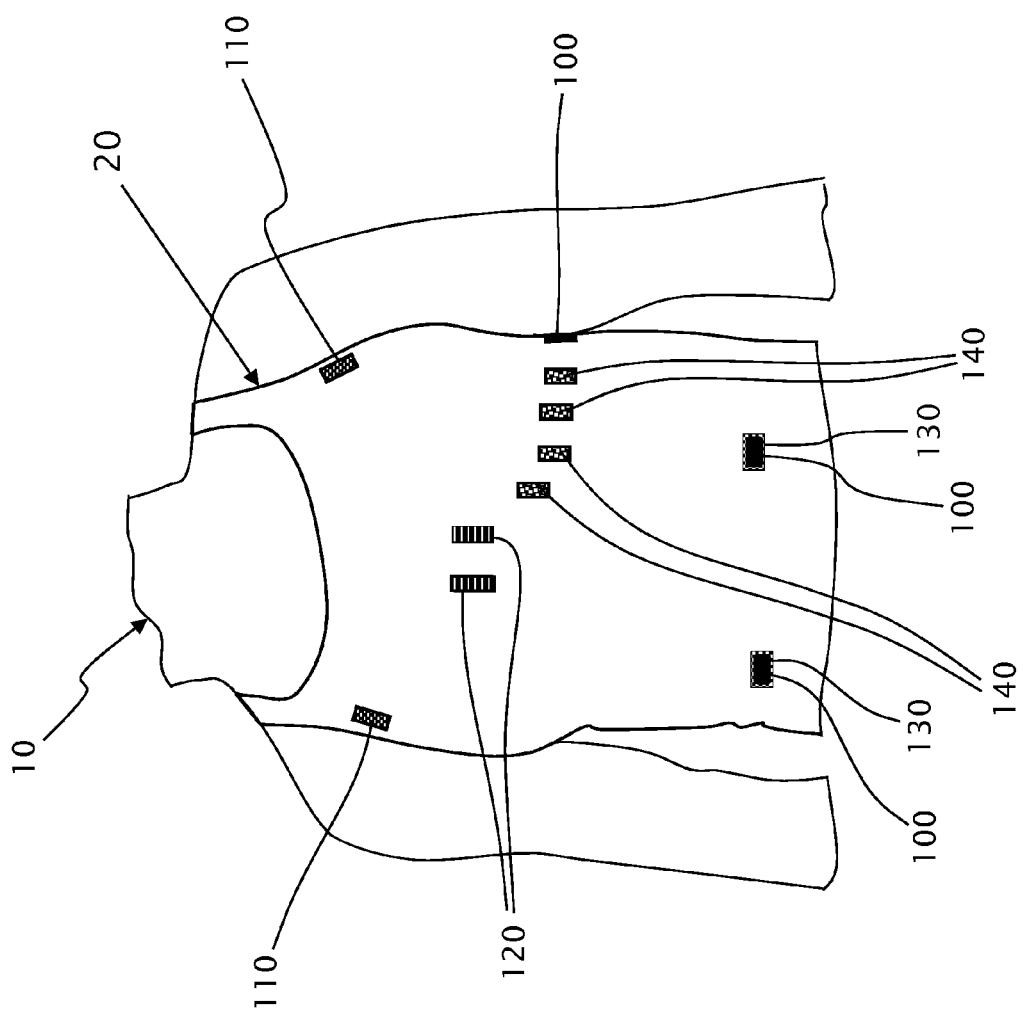
FIG. 1 is a schematic illustration of an exemplary garment, having a tubular form, wherein textile electrodes are knitted therein, and then rigidified according to embodiments of the present invention.

The present invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided, so that this disclosure will be thorough and complete, and will fully convey the scope of the invention to those skilled in the art.

An embodiment is an example or implementation of the inventions. The various appearances of "one embodiment," "an embodiment" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "one embodiment", "an embodiment", "some embodiments" or "other embodiments" means that a particular feature, structure, or characteristic described in connection with the embodiments is included in at least one embodiments, but not necessarily all embodiments, of the inventions. It is understood that the phraseology and terminology employed herein is not to be construed as limiting and are for descriptive purpose only.

Methods of the present invention may be implemented by performing or completing manually, automatically, or a combination thereof, selected steps or tasks. The term "method" refers to manners, means, techniques and procedures for accomplishing a given task including, but not limited to, those manners, means, techniques and procedures either known to, or readily developed from known manners, means, techniques and procedures by practitioners of the art to which the invention belongs. The descriptions, examples, methods and materials presented in the claims and the specification are not to be construed as limiting but rather as illustrative only.

Meanings of technical and scientific terms used herein are to be commonly understood as to which the invention belongs, unless otherwise defined. The present invention can be implemented in the testing or practice with methods and materials equivalent or similar to those described herein.

It should be noted that orientation related descriptions such as "bottom", "up", "horizontal", "vertical", "lower", "top" and the like, assumes that the is worn by a person being in a standing position.

The knitted electrodes in the garment are made of conductive yarns, wherein each conductive yarn is knitted together with other basic yarns such as Nylon, bare spandex, covered spandex and/or other types of yarn. The methods described assume usage of a Santoni knitting machine or an equivalent machine.

The electrodes location and level of pressure of the electrode on the body, in particular for textile electrodes, is critical for measuring electrocardiogram (ECG), electroencephalogram (EEG), electrooculogram (EOG), and other medical parameters. The location, shape, and size of each of the electrodes are critical for good and efficient ECG, EEG, EOG, signals reading, while taking into account the efficiency of ECG reading signals, wearing comfort, correct size for men and women, knitting capabilities, etc. Furthermore, it is critical for measuring ECG, EEG, EOG and other medical parameters, that the spacing among the electrodes remains stable.

FIG. 1 is a schematic illustration of an exemplary knitted smart garment 20, according to embodiments of the present invention, having knitted textile electrodes 100 knitted therein, wherein typically, textile electrodes 100 are interconnected with a processor (not shown) by conductive means (not shown). Knitted smart garment 20 has a tubular form, wherein textile electrodes 100 are knitted integrally therein. The knitted electrodes are located in the selected areas on the fabric based on the desired ECG signals efficiency.

An aspect of the present invention is to provide mean for stabilizing the physical dimensions and the bodily positioning of textile electrodes 100. A first mean to stabilizing the physical dimensions and the bodily positioning of selected textile electrodes 100 is to rigidify these textile electrodes 100. Various types of rigidifying means are shown in FIG. 1. While textile electrode 100 represents a non-rigidified electrode, textile electrodes 110, 120, 130 and 140 represent rigidified electrodes.

Textile electrode 110 represents an electrode rigidified by a film of rigid material such as thermoplastic polyurethane (TPU). Electrode 110 is typically laminated with a rigidifying film on the surface of electrode 110 distal from the skin of the monitored body (referred to herein as the "external surface" of the electrode), according to some embodiment of the present invention. In some embodiments, the external surface of electrode 110 is the side that does not have the knitted terry loops. Typically, there is no need to apply heat or pressure to bond the film.

In some embodiments, special TPU film is used, wherein the film is bonded to the fabric by glue. Optionally, one side of the film has glue applied thereon, and thus, can be glued onto a fabric.

Once the TPU is glued onto selected electrodes, the TPU substantially prevents or at least limits electrodes 110 from stretching and thereby facilitates receiving stable signals reading.

It should be noted that TPU film may have selected colors or may have no color at all.

Textile electrode 120 represents an electrode rigidified by fusible yarn, having a low melting point. The special fusible yarn (white lines in FIG. 1) is knitted together with the electrodes, extending proximally to the external surface of electrode 120.

Typically, when the fabric is dyed, the fusible yarn melts and thereby creates a stable and rigidified area, which prevents or at least limits the elasticity of electrode 120.

The amount of fusible yarn in the electrode is determined by the amount of knitted courses in the electrodes with the fusible yarn.

Textile electrode 130 represents an electrode rigidified by building a rigid zone around selected electrodes 100 forming a rigid frame around the selected electrodes 100, to thereby prevent or at least limit the elasticity of electrode 130, according to some embodiments of the present invention.

The knitted frame is made of yarn having no or limited elasticity, around each electrode, except for the edge connected to a conductive trace or a conductive stipe or a conductive wire.

In one example embodiment, the non-stretchable construction, having a preconfigured width, is knitted around the electrode circumference to form the stable frame. For example, the width is formed using 12 adjacent needles.

When the garment is in use and is stretched, the fabric itself does stretch during wearing, however, the electrodes remain substantially in the same size and position.

Textile electrode 140 represents an electrode rigidified by spraying a special cross polymer lubricant on the external surface of electrode 140, wherein the chemical cross polymer lubricant is absorbed into the yarns of electrode 140 to rigidify electrode 140 and thereby stabilizes the electrodes' dimensions. The special cross polymer lubricant may also be sprayed on selected regions of the garment situated between two adjacent textile electrodes 100.

Preferably, the special lubricant has the ability to stand at least a preconfigured number of washes, a comfort touch and feel of the garment when in touch with the skin and wearing comfort.

Figure 2:
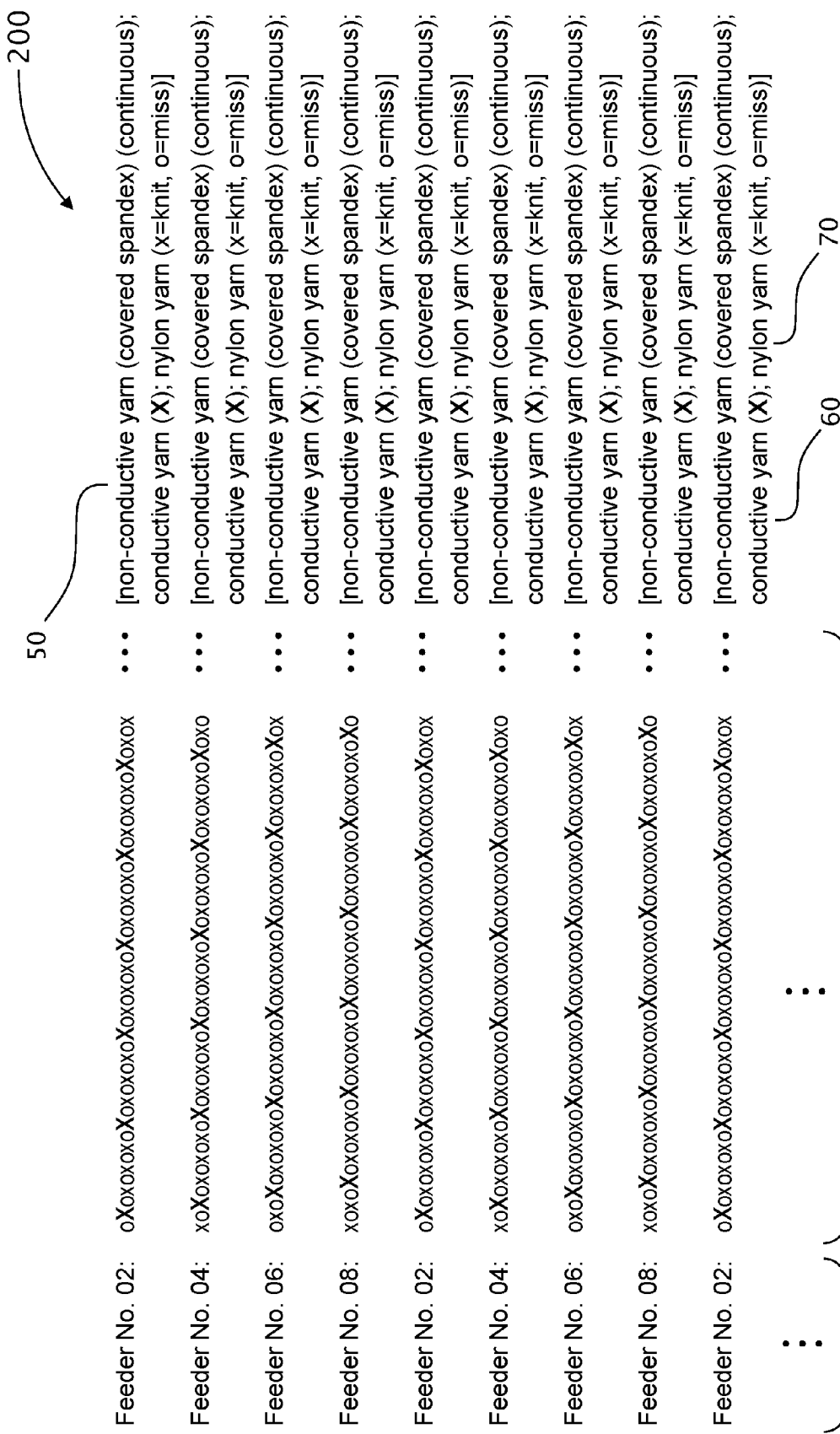
FIG. 2 outlines an example knitting scheme of a conductive electrode designed for a Santoni type knitting machine, according to embodiments of the present invention, wherein the conductive electrode is rigidified with a nylon yarn.

Reference in now made to FIG. 2 that outlines an example knitting scheme 200 of a conductive electrode designed for a Santoni type knitting machine, wherein the conductive electrode is rigidified with a nylon yarn, according to embodiments of the present invention. Thereby, substantially reducing the elasticity of the electrode produced.

It should be noted that in previous electrode knitting constructions, the nylon base-yarn that takes part in the knitting program, is not knitted at the electrode area, but is floating at the back side of the electrode. This is done in order to allow the conductive yarn to create the float loops and be in substantive tangible contact with the body.

In this invention the nylon base-yarn is knitted together with the conductive yarn of the electrode to thereby form a more rigid and stable fabric.

The knitted electrode, as described in FIG. 2, is knitted to form float loops made of the conductive yarns (for example, 70/2 Den by Xstatic), which are designed to float over the fabric surface in the number of needles as designed. The length of the float loop is determines by the number of needles the loop is floating over. This type of knitted textile electrode is described in international patent application PCT/IL2013/050964 ('964), the disclosure of which is incorporated by reference for all purposes and is fully set forth herein.

As described in '964 the length of the float loops, as well as the specific knitting density in the knitted electrode area, and in selected areas in the basic garment, is determined by the desired quality level of ECG signals. Furthermore, the use of float loops in a shifted needle knitting scheme, together with unique digital knitting density control, enables achieving the following important advantages:

Improve the pressure and the tightness of the electrodes to the body which is a critical parameter for good efficient ECG reading Obtaining good conductivity across knitted line segments.

The electrodes are located well in the designated bodily position even when the body is in motion.

The float loop electrodes can penetrate the hair on a hairy skin allowing reaching good ECG signals with no need to remove the hair as it is done today in regular ECG checks.

The float loop electrodes eliminating the use of gel or other wetting material used today to reach ECG signals.

The float-loop electrodes are knitted together in same knitting process of knitting the basic garment and coming out of the machine as a single unit. The tight float-loop knitting scheme produces a rigid electrode with respect to the fabric situated adjacent to the electrode.

However, to further rigidify the float-loop electrode, the present invention, as outlined in FIG. 2, describes an example knitting method 200 of producing a rigid float-loop electrode. In this example embodiment 200, the conductive yarn is made of Nylon covered with silver or stainless steel, knitted on an 8-feeds Santoni type circular knitting machine (or machines with equivalent capabilities), together with the non-conductive yarns: covered Spandex 50 (and/or bare spandex). In this example embodiment, the knitting scheme 210 is designed for a 4 (four) feeds system, but is using in the example shown, with no limitations, an 8 (eight) feed Santoni type knitting machine, according to variations of the present invention. The 4 feeders knit four knitted lines, being four loops of the continuous knitting spiral, including respective line segments of each electrode that is situated on the garment section being knitted.

In this embodiment, in all the knitting courses, the float loops that are formed from the conductive yarn 60, that float over 7 needles, as can be seen and appreciated by a person skilled in the art in FIG. 2, while the non-conductive covered (or optionally, bared) spandex 50 is knitted continuously in the same knitted course. It should be noted that, in this embodiment, the base-yarn is referred to, with no limitations, as a nylon base-yarn.

In the example shown in FIG. 2, four out of eight available feeders are used: feeders 1, 3, 5 and 7 are not used, while feeders 2, 4, 6 and 8 are used. Generally, the same knitting scheme 210 is used in all courses. However, the float-loop stitch starting needle $D_j$ in Feeder i+2 is shifted by s needles with respect to the float-loop stitch starting needle in Feeder i. In the example shown in FIG. 4, s=1.

The present invention is not limited to the knitting parameters shown in the example as illustrated in FIG. 2 and corresponding description in the specifications. The example as illustrated in FIG. 2 exemplifies methods for knitting a garment 20 having a tubular form, including knitting at least one conductive textile electrode, using a knitting machine having N feeders and M needles.

In one embodiment the method includes continuously knitting a tubular form 20 with a flexible non-conductive yarn 50 and a nylon base-yarn 70, knitting the at least one textile electrode integrally within tubular form 20, using a conductive yarn 60, in addition to the non-conductive yarns. However, in the electrode region, nylon base-yarn 70 is preferably knitted in a knit-and-miss scheme. The nylon base-yarn 70 may be knitted in a continuous or a knit-and-miss scheme, wherein the knit-and-miss may be in any combination, including knit one and miss one (knit-one-andmiss-one), knit two and skip one (knit-two-and-miss-one), knit one and skip two (knit-one-and-miss-two) and so on and so forth.

The conductive yarn 60 is knitted in a float-loop form by knitting a stitch and then skipping over y needles, as follows:
i) knitting a course k, being a line segment $L_k$, using feeder $F_i$ and starting at needle $D_j$, wherein the next float-loop starting stitch is at y needles away from the starting stitch needle of the previous float-loop;
ii) knitting line segment $L_{k+1}$, using the next participating feeder and starting stitching the first float-loop with needle $D_{j+s}$, where $0 \leq s < y$ and typically j=1; and
iii) repeat steps (i) and (ii) for a preconfigured length of the tubular form 20, i.e. a preconfigured number of knitting courses.

It should be noted that each line segment has a preconfigured length.

It should be further noted that a preconfigured number of feeders of the knitting machine participate in the knitting process of the garment.

Figure 3B:
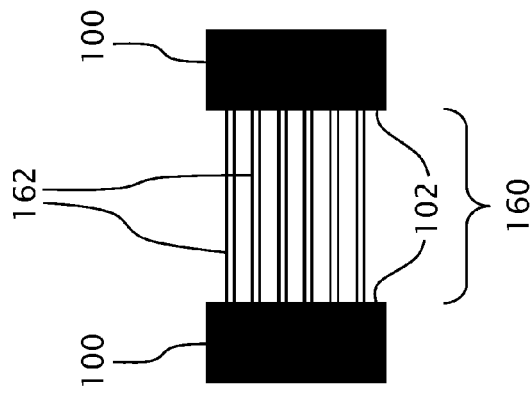
FIG. 3b is a schematic detailed illustration of a textile structure (160).
Figure 3A:
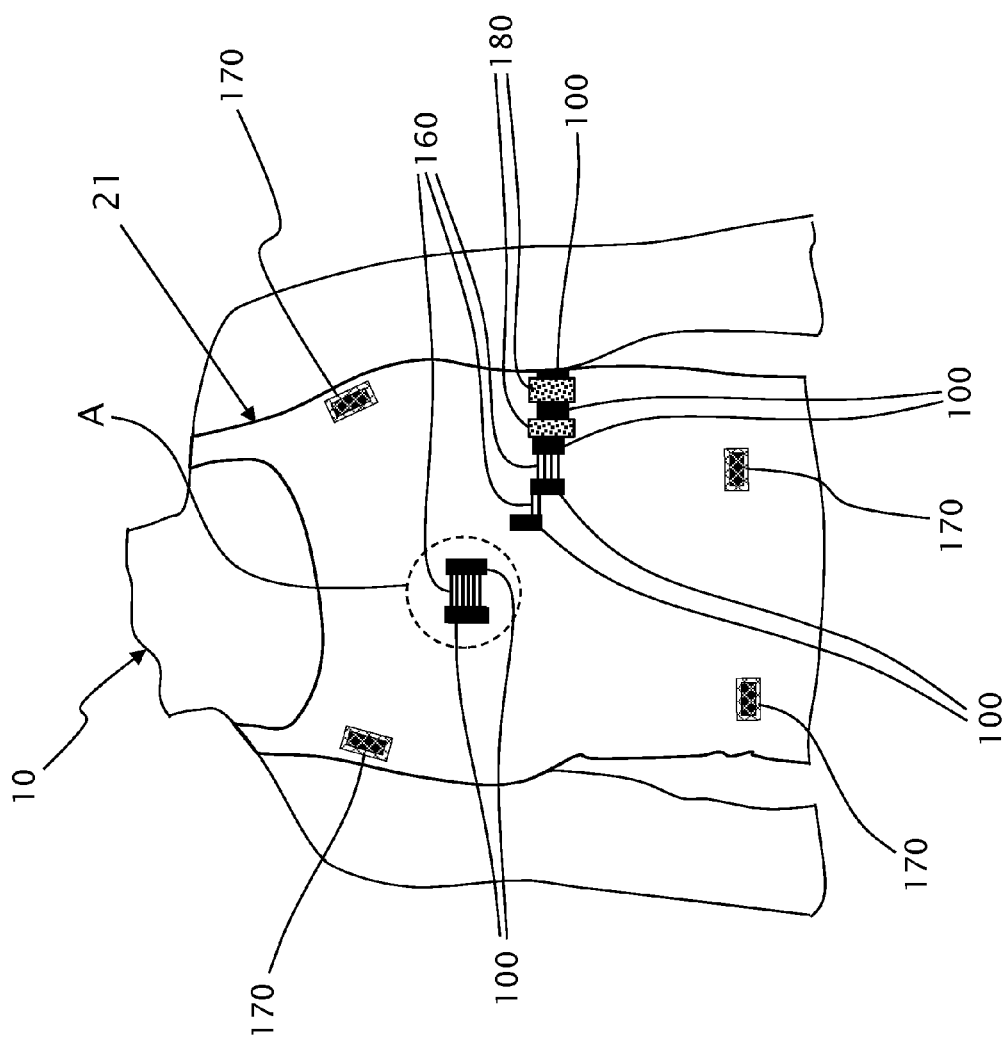
FIG. 3a is a schematic illustration of an exemplary garment, having a tubular form, wherein textile electrodes are knitted therein, and wherein regions of the garment, immediately adjacent to the textile electrodes, are rigidified or loosened, according to some embodiments of the present invention.

Reference is now made to FIG. 3a, a schematic illustration of an exemplary garment 21, having a tubular form, wherein textile electrodes 100 are knitted therein, and wherein regions of garment 21, immediately adjacent to textile electrodes 100, are rigidified or loosened, according to some embodiments of the present invention.

Various types of rigidifying means are shown in FIG. 3a. While textile electrode 100 represents a non-rigidified electrode, selected regions 160, 170 and 180 represent rigidified electrodes or rigidified selected regions that rigidify adjacent to electrodes.

Textile structure 160, also shown in details in FIG. 3b, represents a knitted structure for maintaining a substantially stable distance between horizontally adjacent electrodes 100, wherein non-elastic threads 162 are knitted in between selected horizontally adjacent electrodes 100, according to some embodiment of the present invention.

At least one substantially non-elastic thread 162 is knitted to interconnect the proximal vertical edges 102 of horizontally adjacent electrodes 100, wherein a certain amount of allowable controlled suspension is given to each electrode 100 according to the expected body dimensions of the wearer. Similarly, a special thread may be knitted to interconnect proximal horizontal edges of vertically adjacent electrodes 100.

When the knitted garment 21 is stretched on a monitored body (such as in the wearing process), non-elastic thread 162, knitted between electrodes 100, is suspended to a preconfigured distance, while electrodes 100 maintain a stable and substantially equal relative distance among the pair of electrodes 100.

Non-elastic thread 162 may be a Nylon or Polyester yarn with limited elasticity.

Textile structure 180 represents a structure for maintaining a substantially stable distance between horizontally adjacent electrodes 100, wherein the space in between horizontally adjacent electrodes 110 is rigidified by a film of rigid material such as TPU. Electrode 100 is typically laminated with a rigidifying film on the external surface of electrode 100, according to some embodiment of the present invention. Typically, there is no need to apply heat or pressure to bond the film. The film of rigid material may also be laminated over fabric regions in between vertically adjacent electrodes 100.

A second mean to stabilizing the physical dimensions and the bodily positioning of textile electrodes 100 is to loosen loosened regions disposed adjacent to selected textile electrodes 100. Textile structure 190 provide loosened regions adjacent to selected electrodes 100, typically isolated electrodes 100, such as LA/RA (Left Arm/Right Arm) ECG electrodes. Loosened region 190 provide a protecting barrier near or around an isolated electrodes 100 that is situation at or proximal to a bodily region that is prone to motion artifact. For example LA/RA ECG electrodes tend to move with respect to the adjacent skin area due to the motion of the respective arms. Such motion of the respective arms form pulling forces within the garment regions that are near the arms. By, loosening the knitting density around such electrodes 100, the respective adjacent loosened region absorbs much of these pulling forces to thereby prevent the absorbed pulling forces from reaching electrodes 100, to thereby prevent the formation of motion artifact in the signal sensed by the respective textile electrode 100. As illustrated in FIG. 3a knitted garment 21 includes at least one laminated structure 180 for substantially reducing the elasticity of the space in between horizontally adjacent electrodes 100. The TPU film, having limited stretchability, is laminated on the region of garment 21 between selected electrodes 100.

When the garment 100 is stretched during wearing, the laminated regions 180 between horizontally adjacent electrodes 100 are stretched to a preconfigured distance in between electrodes 100, as allowed by the TPU film, and thereby keep the selected pair of electrodes 100 in the preconfigured relative positioning, and prevent further stretching.

As illustrated in FIG. 3a knitted garment 21 includes at least one structure 170 for substantially reducing the elasticity of an electrode 100 and the garment fabric surrounding that electrode 100, according to some embodiment of the present invention, wherein a safety net is built around that electrode 100 or is sewn in between selected adjacent electrodes 100.

A non-elastic yarn, with limited stretchability, is sewn over an electrode 100 and/or in between selected adjacent electrodes 100.

When the garment 100 is stretched during wearing, the sewn structure 170 is suspended to a preconfigured distance and stops the electrodes 100 from stretching further, while the garment (21) itself continues to stretch.

This will hold and ensure the relative positioning of each of the selected electrodes 100 with respective to each other.

When structure 170 is sewn as safety net over and around a selected electrode 100, structure 170 rigidifies the selected electrode 100.

The invention being thus described in terms of embodiments and examples, it will be obvious that the same may be varied in many ways. Such variations are not to be regarded as a departure from the spirit and scope of the invention, and all such modifications as would be obvious to one skilled in the art are intended to be included within the scope of the claims.

What is claimed is:

1. A method for stabilizing the physical dimensions and positioning of at least one selected textile region of a knitted garment, the method comprising the steps of:
   a) knitting the garment in a tubular form with a preconfigured knitting density, wherein at least one conductive textile electrode is integrally knitted into the garment, while knitting the garment;
   b) rigidifying at least one of said at least one selected textile region, thereby substantially reducing the elasticity of said at least one selected textile region; and
   c) knitting a preconfigured region proximal to said at least one selected textile region with a lower knitting density than said preconfigured density of said tubular form, to thereby form a loosened said region in said proximity to said at least one selected textile region.

2. The textile region stabilizing method as in claim 1, wherein said at least one selected textile region is said at least one conductive textile electrode.

3. The textile region stabilizing method as in claim 1, wherein said rigidifying includes applying rigidifying matter onto and/or into said at least one selected textile region.

4. The textile region stabilizing method as in claim 3, wherein said rigidifying matter is thermoplastic polyurethane (TPU), and wherein said TPU is laminated over the external surface of said at least one selected textile region.

5. The textile region stabilizing method as in claim 3, wherein said rigidifying matter is fusible yarn having a low melting point;
wherein said fusible yarn is knitted over the external surface of said at least one selected textile region; and
wherein when the fabric of said garment is dyed, said fusible yarn melts and thereby creates a stable and rigidified area.

6. The textile region stabilizing method as in claim 3, wherein said rigidifying matter is a non-elastic yarn having no or limited elasticity, and wherein a frame, having a preconfigured width, is knitted around said at least one selected textile region, using said non-elastic yarn.

7. The textile region stabilizing method as in claim 3, wherein said rigidifying matter is a non-elastic yarn having no or limited elasticity, and wherein said non-elastic yarn is knitted in said region of said garment between two adjacent textile electrodes.

8. The textile region stabilizing method as in claim 3, wherein said rigidifying matter is a non-elastic yarn having no or limited elasticity, and wherein said non-elastic yarn is sewn over said at least one selected textile region.

9. The textile region stabilizing method as in claim 3 further comprising the step of modifying the elasticity of at least one other selected region of the garment.

10. The textile region stabilizing method as in claim 2, wherein said rigidifying includes knitting said at least one textile electrode with higher knitting density than said preconfigured knitting density of said tubular form.

11. A method for knitting a garment having a tubular form being knitted with a base-yarn, including knitting at least one conductive textile electrode, using a knitting machine having N participating feeders and M needles, the method comprising the steps of:
a) continuously knitting said tubular form with one or more flexible non-conductive base-yarns and with a preconfigured knitting density; and
b) knitting said at least one textile electrode integrally within said tubular form, using a conductive yarn, in addition to said non-conductive yarns, wherein said conductive yarn is knitted in a float-loop form by knitting a stitch and skipping over y needles, as follows:
i) continue knitting with at least one base-yarn, when start knitting a current line segment of a conductive textile electrode;
ii) knitting a line segment $L_k$, using feeder $F_i$ and start stitching with needle $D_j$;
iii) knitting line the next segment $L_{k+1}$, using the next feeder $F_{i+1}$ and start stitching the first float-loop with needle $D_{j+s}$, where 0<s<y;
iv) repeat steps (i) and (ii) for N feeders and for a preconfigured number of line segments, wherein each line segment has a preconfigured length; and
v) resume knitting with the base-yarns, when completed knitting said current line segment,
wherein said float-loops are knitted in a shifted needle knitting scheme, together with unique digital knitting density control, to thereby improve the pressure and the tightness of said at least one conductive textile electrode to the skin of the user; and
wherein a preconfigured region, proximal to said at least one conductive textile electrode, is knitted with a lower knitting density than said preconfigured density of said tubular form, to thereby form a loosened region in said proximity to said at least one conductive textile electrode.

12. The knitting method as in claim 11, wherein said continued knitting with at least one base-yarn is knitted in a knit-and-miss knitting scheme, to thereby modify the elasticity of at least one conductive textile electrode of a knitted garment.

13. The knitting method as in claim 11, wherein j=1.

14. A garment having a tubular form, being knitted by a seamless knitting machine with base-yarns, the garment comprising at least one conductive textile electrode, said at least one conductive textile electrode comprising a multiplicity of knitted line segments, each knitted with a conductive yarn and a spandex yarn,
wherein said spandex yarn is knitted continuously;
wherein at least one of said base-yarns continues knitting when start knitting a current line segment of a conductive textile electrode, in a knit-and-miss knitting scheme;
wherein said conductive yarn has a float-loop form, forming a multiplicity of said float-loops;
wherein each of said float-loops is knitted by skipping over y needles between consecutive stitches; and
wherein a given of said line segments starts stitching by needle $D_j$, and the next of said line segments starts stitching by needle $D_{j+s}$, where 0<s<y,
wherein said tubular form is knitted with a preconfigured knitting density; and
wherein a preconfigured region, proximal to said at least one conductive textile electrode, is knitted with a lower knitting density than said preconfigured density of said tubular form, to thereby form a loosened region in said proximity to said at least one conductive textile electrode.

15. The garment as in claim 14, wherein said at least one textile electrode is knitted with higher knitting density than said preconfigured knitting density of said tubular form.

16. The garment as in claim 14, wherein at least one conductive textile electrode is rigidified by applying rigidifying matter onto said at least one conductive textile electrode.

17. The garment as in claim 16, wherein said at least one conductive textile electrode is rigidified using TPU, and wherein said TPU is laminated over the external surface of said at least one conductive textile electrode.

18. The garment as in claim 16, wherein said at least one conductive textile electrode is rigidified using fusible yarn having a low melting point,
wherein said a fusible yarn is knitted over the external surface of said at least one conductive textile electrode; and
wherein when said garment is dyed, said fusible yarn melts and thereby creates a stable and rigidified area.

19. The garment as in claim 16, wherein said at least one conductive textile electrode is rigidified using a non-elastic yarn having no or limited elasticity.

20. The garment as in claim 16, wherein said rigidifying matter is a cross polymer lubricant, and wherein said cross polymer lubricant is sprayed over in said at least one conductive textile electrode.

* * * * *